(12) United States Patent
Nelson et al.

(10) Patent No.: US 11,905,341 B2
(45) Date of Patent: Feb. 20, 2024

(54) SOLVENT-BASED PROCESSES FOR PRODUCING NANOCELLULOSE, AND COMPOSITIONS AND PRODUCTS PRODUCED THEREFROM

(71) Applicant: GranBio Intellectual Property Holdings, LLC, Minnetrista, MN (US)

(72) Inventors: Kimberly Nelson, Atlanta, GA (US); Theodora Retsina, Atlanta, GA (US); Vesa Pylkkanen, Atlanta, GA (US); Ryan O'Connor, Minnetrista, MN (US)

(73) Assignee: GranBio Intellectual Property Holdings, LLC, Thomaston, GA (US)

( * ) Notice: Subject to any disclaimer, the term of this patent is extended or adjusted under 35 U.S.C. 154(b) by 0 days.

(21) Appl. No.: 17/570,599

(22) Filed: Jan. 7, 2022

(65) Prior Publication Data

US 2022/0127382 A1 Apr. 28, 2022

Related U.S. Application Data

(63) Continuation of application No. 15/644,878, filed on Jul. 10, 2017, now abandoned.

(60) Provisional application No. 62/362,101, filed on Jul. 14, 2016.

(51) Int. Cl.
| | | |
|---|---|---|
| *C08B 15/08* | (2006.01) | |
| *C08L 1/02* | (2006.01) | |
| *C08H 8/00* | (2010.01) | |
| *C08B 15/02* | (2006.01) | |
| *D21C 3/04* | (2006.01) | |
| *D21C 3/20* | (2006.01) | |
| *D21C 5/00* | (2006.01) | |
| *D21C 9/00* | (2006.01) | |
| *D21H 11/18* | (2006.01) | |
| *C12P 7/10* | (2006.01) | |
| *C12P 19/02* | (2006.01) | |

(52) U.S. Cl.
CPC .............. *C08B 15/08* (2013.01); *C08B 15/02* (2013.01); *C08H 8/00* (2013.01); *C08L 1/02* (2013.01); *D21C 3/04* (2013.01); *D21C 3/20* (2013.01); *D21C 5/005* (2013.01); *D21C 9/007* (2013.01); *D21H 11/18* (2013.01); *C12P 7/10* (2013.01); *C12P 19/02* (2013.01); *C12P 2201/00* (2013.01); *C12P 2203/00* (2013.01); *Y02E 50/10* (2013.01); *Y02E 50/30* (2013.01); *Y02P 20/54* (2015.11)

(58) Field of Classification Search
CPC ........... C08B 15/08; C08B 15/02; C08H 8/00; C08L 1/02; D21C 3/04
See application file for complete search history.

(56) References Cited

U.S. PATENT DOCUMENTS

| | | | | |
|---|---|---|---|---|
| 2015/0184345 A1* | 7/2015 | Nelson | ..................... | D21C 3/06 435/165 |
| 2015/0259709 A1* | 9/2015 | Retsina | ..................... | C12P 7/14 435/162 |
| 2016/0168343 A1* | 6/2016 | Retsina | .................... | D01C 1/00 106/163.01 |

* cited by examiner

*Primary Examiner* — Leigh C Maier
*Assistant Examiner* — Everett White
(74) *Attorney, Agent, or Firm* — O'Connor & Company; Ryan P. O'Connor

(57) ABSTRACT

The present invention provides a process for producing a nanocellulose material, comprising: fractionating a lignocellulosic biomass feedstock in the presence of a solvent for lignin and water, but no acid catalyst, to generate cellulose-rich solids; and then mechanically treating the cellulose-rich solids to form a nanocellulose material comprising cellulose nanofibrils and/or cellulose nanocrystals. Many organic or inorganic solvents are possible. In some embodiments, the solvent for lignin is an oxygenated organic compound, such as a $C_1$-$C_{18}$ alcohol, e.g. ethanol, ethylene glycol, propanol, propanediol, glycerol, butanol, or butanediol. The solvent for lignin may be an aromatic alcohol, such as phenol, cresol, or benzyl alcohol. The solvent for lignin may be a ketone, an aldehyde, or an ether, such as methyl ethyl ketone or diethyl ether. The solvent for lignin may be a non-oxygenated alkane, olefin, or aromatic hydrocarbon. In some embodiments, the solvent for lignin is an ionic liquid.

20 Claims, 2 Drawing Sheets

SOLVENT-BASED PROCESSES FOR PRODUCING NANOCELLULOSE, AND COMPOSITIONS AND PRODUCTS PRODUCED THEREFROM

PRIORITY DATA

This patent application is a continuation of U.S. patent application Ser. No. 15/644,878, filed on Jul. 10, 2017, which claims priority to U.S. Provisional Patent App. No. 62/362,101, filed on Jul. 14, 2016, each of which is hereby incorporated by reference herein.

FIELD

The present invention generally relates to nanocellulose and related materials produced by fractionating lignocellulosic biomass and further processing the cellulose fraction.

BACKGROUND

Biomass refining (or biorefining) has become more prevalent in industry. Cellulose fibers and sugars, hemicellulose sugars, lignin, syngas, and derivatives of these intermediates are being utilized for chemical and fuel production. Indeed, we now are observing the commercialization of integrated biorefineries that are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint.

Lignocellulosic biomass is the most abundant renewable material on the planet and has long been recognized as a potential feedstock for producing chemicals, fuels, and materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network. Some forms of biomass (e.g., recycled materials) do not contain hemicellulose.

Despite being the most available natural polymer on earth, it is only recently that cellulose has gained prominence as a nanostructured material, in the form of nanocrystalline cellulose (NCC), nanofibrillar cellulose (NFC), and bacterial cellulose (BC). Nanocellulose is being developed for use in a wide variety of applications such as polymer reinforcement, anti-microbial films, biodegradable food packaging, printing papers, pigments and inks, paper and board packaging, barrier films, adhesives, biocomposites, wound healing, pharmaceuticals and drug delivery, textiles, water-soluble polymers, construction materials, recyclable interior and structural components for the transportation industry, rheology modifiers, low-calorie food additives, cosmetics thickeners, pharmaceutical tablet binders, bioactive paper, pickering stabilizers for emulsion and particle stabilized foams, paint formulations, films for optical switching, and detergents. Despite the major advantages of nanocellulose such as its non-toxicity and great mechanical properties, its use to now has been in niche applications. Its moisture sensitivity, its incompatibility with oleophilic polymers, and the high energy consumption needed to produce, for example, NFC have so far prevented it from competing with other mass products such as ordinary paper or plastic. See "THE GLOBAL MARKET FOR NANOCELLULOSE TO 2017," FUTURE MARKETS INC. TECHNOLOGY REPORT No. 60, SECOND EDITION (Oct. 2012).

Biomass-derived pulp may be converted to nanocellulose by mechanical processing. Although the process may be simple, disadvantages include high energy consumption, damage to fibers and particles due to intense mechanical treatment, and a broad distribution in fibril diameter and length.

Biomass-derived pulp may be converted to nanocellulose by chemical processing. For example, pulp may be treated with 2,2,6,6-tetramehylpiperidine-1-oxy radical (TEMPO) to produce nanocellulose. Such a technique reduces energy consumption compared to mechanical treatment and can produce more uniform particle sizes, but the process is not regarded as economically viable.

Improved processes for producing nanocellulose from biomass at reduced energy costs are needed in the art. Also, improved starting materials (i.e., biomass-derived pulps) are needed in the art for producing nanocellulose. It would be particularly desirable for new processes to possess feedstock flexibility and process flexibility to produce either or both nanofibrils and nanocrystals, as well as to co-produce sugars, lignin, and other co-products. For some applications, it is desirable to produce hydrophobic nanocellulose.

SUMMARY

In some variations, the present invention provides a process for producing a nanocellulose material, the process comprising:

(a) providing a lignocellulosic biomass feedstock;

(b) fractionating the feedstock in the presence of a solvent for lignin and water, but no acid catalyst, to generate cellulose-rich solids and a liquid containing hemicellulose and lignin;

(c) mechanically treating the cellulose-rich solids to form a nanocellulose material comprising cellulose nanofibrils and/or cellulose nanocrystals, and (d) recovering the nanocellulose material.

Many solvents are possible. The solvent for lignin may be an organic compound or an inorganic compound. In some embodiments, the solvent for lignin is an oxygenated organic compound, such as an aliphatic alcohol. The aliphatic alcohol may be a $C_1$-$C_{18}$ alcohol, such as methanol, ethanol, ethylene glycol, 1-propanol, 2-propanol, propanediol, glycerol, 1-butanol, 2-butanol, isobutanol, butanediol, 1-pentanol, 1-hexanol, or cyclohexanol. In some embodiments, the solvent for lignin is an aromatic alcohol, such as phenol, cresol, benzyl alcohol, or derivatives, analogues, or combinations thereof. In some embodiments, the solvent for lignin is a ketone, an aldehyde, an ether, or a combination thereof, such as methyl ethyl ketone or diethyl ether. In some embodiments, the solvent for lignin is a non-oxygenated alkane, olefin, or aromatic hydrocarbon, or a combination thereof. In some embodiments, the solvent for lignin is an ionic liquid.

Generally, the solvent for lignin may be water-soluble, forming a single phase with the water in the digestor and/or after fractionation. Or the solvent for lignin may form a separate phase from the water (or from a water-rich phase comprising the water) in the digestor and/or after fractionation (i.e. at reduced temperature compared to the digestor temperature).

In some embodiments, during step (c), the cellulose-rich solids are treated with a total mechanical energy of less than about 5000 kilowatt-hours per ton of the cellulose-rich solids, less than about 2000 kilowatt-hours per ton of the cellulose-rich solids, or less than about 1000 kilowatt-hours per ton of the cellulose-rich solids.

In some embodiments, mechanical treating in step (c) further comprises treatment of the cellulose-rich solids with one or more acids, such as sulfur dioxide, sulfurous acid, lignosulfonic acid, acetic acid, formic acid, or combinations thereof. In some embodiments, mechanical treating in step (c) further comprises treatment of the cellulose-rich solids with one or more enzymes. In some embodiments, step (c) does not employ any enzymes or acids but optionally includes treatment of the cellulose-rich solids with heat.

The process further may include bleaching the cellulose-rich solids prior to step (c) and/or as part of step (c). The process alternatively or additionally may include bleaching the nanocellulose material during step (c) and/or following step (c).

The crystallinity of the nanocellulose material is at least 60%, in some embodiments.

In some preferred embodiments, the nanocellulose material is at least partially hydrophobic via deposition of at least some of the lignin onto a surface of the cellulose-rich solids during step (b). In these or other embodiments, the nanocellulose material is at least partially hydrophobic via deposition of at least some of the lignin onto a surface of the nanocellulose material during step (c) or step (d). Lignin that is not utilized in this way may later be recovered, combusted, or further treated.

The process of some embodiments further comprises hydrolyzing amorphous cellulose into glucose in step (b) and/or step (c), recovering the glucose, and optionally fermenting the glucose to a fermentation product. Optionally, the process further comprises recovering, fermenting, or further treating hemicellulosic sugars derived from the hemicellulose. In certain embodiments, the hemicellulosic sugars may be fermented (or chemically converted) to produce a monomer or precursor thereof; polymerizing the monomer to produce a polymer; and combining the polymer and the nanocellulose material to form a polymer-nanocellulose composite.

In some embodiments of the invention, the process further comprises chemically converting the nanocellulose material to one or more nanocellulose derivatives. Such nanocellulose derivatives may be selected from the group consisting of nanocellulose esters, nanocellulose ethers, nanocellulose ether esters, alkylated nanocellulose compounds, cross-linked nanocellulose compounds, acid-functionalized nanocellulose compounds, base-functionalized nanocellulose compounds, and combinations thereof.

Some variations provide a process for producing a hydrophobic nanocellulose material, the process comprising:

(a) providing a lignocellulosic biomass feedstock;

(b) fractionating the feedstock in the presence of a solvent for lignin and water, but no acid catalyst, to generate cellulose-rich solids and a liquid containing hemicellulose and lignin, wherein a portion of the lignin deposits onto a surface of the cellulose-rich solids, thereby rendering the cellulose-rich solids at least partially hydrophobic;

(c) mechanically treating the cellulose-rich solids to form a nanocellulose material comprising cellulose nanofibrils and/or cellulose nanocrystals; and (d) recovering the hydrophobic nanocellulose material.

Some variations provide a process for producing a nanocellulose-containing product, the process comprising:

(a) providing a lignocellulosic biomass feedstock;

(b) fractionating the feedstock in the presence of a solvent for lignin and water, but no acid catalyst, to generate cellulose-rich solids and a liquid containing hemicellulose and lignin;

(c) mechanically treating the cellulose-rich solids to form a nanocellulose material comprising cellulose nanofibrils and/or cellulose nanocrystals; and (d) incorporating at least a portion of the nanocellulose material into a nanocellulose-containing product.

In some embodiments, the nanocellulose material is at least partially hydrophobic via deposition of at least some of the lignin onto a surface of the cellulose-rich solids during step (b). The nanocellulose material may be made at least partially hydrophobic via deposition of at least some of the lignin onto a surface of the nanocellulose material during step (c) or step (d), i.e., after the digestor. A combination may be employed, in which some lignin is deposited onto (or into) cellulose fibers in the digestor, and then during or following mechanical treatment, more lignin is deposited onto (or into) the refined cellulose, to make hydrophobic nanocellulose.

In some embodiments, the nanocellulose-containing product consists essentially of the nanocellulose material. Many nanocellulose-containing products are possible. In some embodiments, step (d) comprises forming a structural object that includes the nanocellulose material, or a derivative thereof. In some embodiments, step (d) comprises forming a foam or aerogel that includes the nanocellulose material, or a derivative thereof. In some embodiments, step (d) comprises combining the nanocellulose material, or a derivative thereof, with one or more other materials to form a composite. The one or more other materials may include carbon or a polymer selected from polyolefins, polyesters, polyurethanes, polyamides, or combinations thereof, for example. In some embodiments, step (d) comprises forming a film comprising the nanocellulose material, or a derivative thereof. In some embodiments, wherein step (d) comprises forming a coating or coating precursor comprising the nanocellulose material, or a derivative thereof. In some embodiments, the nanocellulose-containing product is configured electrochemically for carrying or storing an electrical current or voltage. In some embodiments, the nanocellulose-containing product is incorporated into a filter, membrane, or other separation device. In some embodiments, the nanocellulose-containing product is incorporated as an additive into a coating, paint, or adhesive. In some embodiments, the nanocellulose-containing product is configured as a catalyst, catalyst substrate, or co-catalyst. In some embodiments, the nanocellulose-containing product is incorporated as a cement additive or concrete additive. In some embodiments, wherein the nanocellulose-containing product is a paper coating. In some embodiments, the nanocellulose-containing product is incorporated as a thickening agent or rheological modifier. In some embodiments, the nanocellulose-containing product is incorporated as an additive in a drilling fluid, a fracturing fluid, an oil recovery fluid, a gas recovery fluid, or combinations thereof.

DETAILED DESCRIPTION OF SOME EMBODIMENTS

Figure 1:
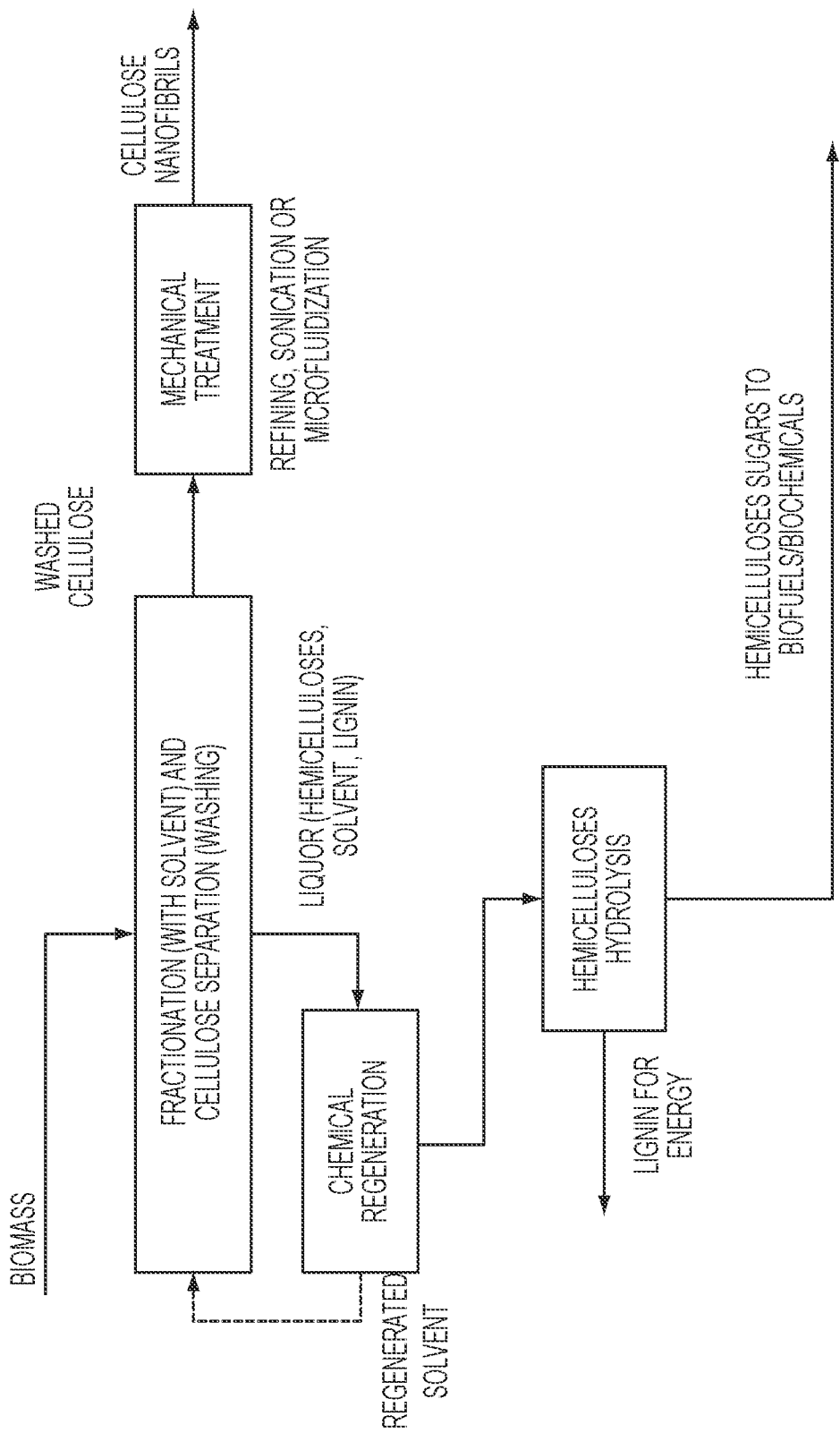
FIG. 1 depicts the production of nanocellulose materials from biomass, according to some embodiments of the invention.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing parameters, reaction conditions, concentrations of components, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

Generally it is beneficial to process biomass in a way that effectively separates the major fractions (cellulose, hemicellulose, and lignin) from each other. The cellulose can be subjected to further processing to produce nanocellulose. Fractionation of lignocellulosics leads to release of cellulosic fibers and opens the cell wall structure by dissolution of lignin and hemicellulose between the cellulose microfibrils. The fibers become more accessible for conversion to nanofibrils or nanocrystals. Hemicellulose sugars can be fermented to a variety of products, such as ethanol, or converted to other chemicals. Lignin from biomass has value as a solid fuel and also as an energy feedstock to produce liquid fuels, synthesis gas, or hydrogen; and as an intermediate to make a variety of polymeric compounds. Additionally, minor components such as proteins or rare sugars can be extracted and purified for specialty applications.

As intended herein, "nanocellulose" is broadly defined to include a range of cellulosic materials, including but not limited to microfibrillated cellulose, nanofibrillated cellulose, microcrystalline cellulose, nanocrystalline cellulose, and particulated or fibrillated dissolving pulp. Typically, nanocellulose as provided herein will include particles having at least one length dimension (e.g., diameter) on the nanometer scale.

"Nanofibrillated cellulose" or equivalently "cellulose nanofibrils" means cellulose fibers or regions that contain nanometer-sized particles or fibers, or both micron-sized and nanometer-sized particles or fibers. "Nanocrystalline cellulose" or equivalently "cellulose nanocrystals" means cellulose particles, regions, or crystals that contain nanometer-sized domains, or both micron-sized and nanometer-sized domains. "Micron-sized" includes from 1 µm to 100 µm and "nanometer-sized" includes from 0.01 nm to 1000 nm (1 µm). Larger domains (including long fibers) may also be present in these materials.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for purposes of illustrating some embodiments only.

Figure 2:
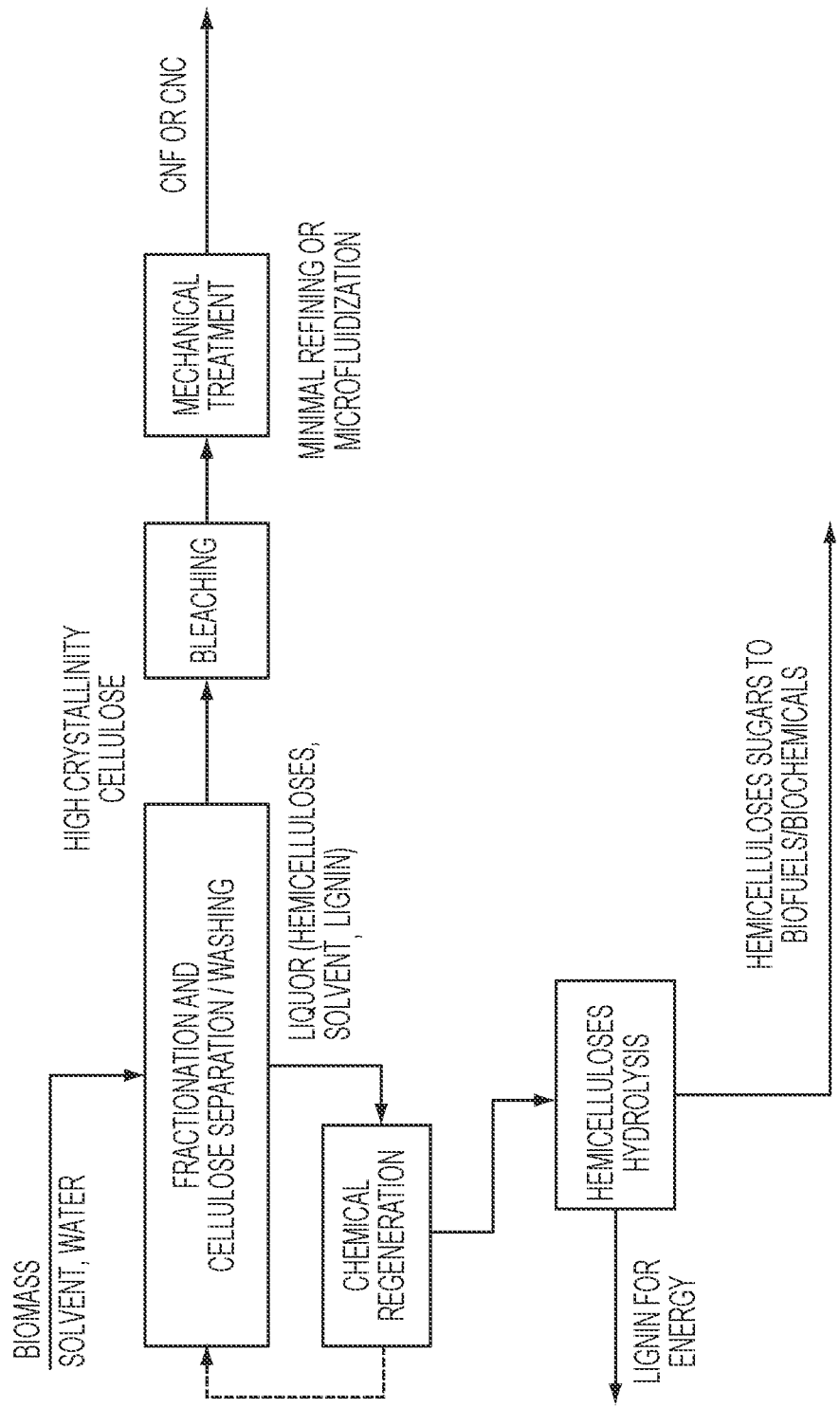
FIG. 2 depicts the production of nanocellulose materials from biomass, according to some embodiments of the invention.

Some process variations may be understood with reference to FIGS. 1-2. Dotted lines denote optional streams. Various embodiments will now be further described, without limitation as to the scope of the invention. These embodiments are exemplary in nature.

In some variations, the present invention provides a process for producing a nanocellulose material, the process comprising:

(a) providing a lignocellulosic biomass feedstock;

(b) fractionating the feedstock in the presence of a solvent for lignin and water, but no acid catalyst, to generate cellulose-rich solids and a liquid containing hemicellulose and lignin;

(c) mechanically treating the cellulose-rich solids to form a nanocellulose material comprising cellulose nanofibrils and/or cellulose nanocrystals, and (d) recovering the nanocellulose material.

Many solvents are possible. The solvent for lignin may be an organic compound or an inorganic compound. In some embodiments, the solvent for lignin is an oxygenated organic compound, such as an aliphatic alcohol. The aliphatic alcohol may be a $C_1$-$C_{18}$ alcohol, such as methanol, ethanol, ethylene glycol, 1-propanol, 2-propanol, propanediol, glycerol, 1-butanol, 2-butanol, isobutanol, butanediol, 1-pentanol, 1-hexanol, or cyclohexanol. In some embodiments, the solvent for lignin is an aromatic alcohol, such as phenol, cresol, benzyl alcohol, or derivatives, analogues, or combinations thereof. In some embodiments, the solvent for lignin is a ketone, an aldehyde, an ether, or a combination thereof, such as methyl ethyl ketone or diethyl ether. In some embodiments, the solvent for lignin is a non-oxygenated alkane, olefin, or aromatic hydrocarbon, or a combination thereof. In some embodiments, the solvent for lignin is an ionic liquid.

Generally, the solvent for lignin may be water-soluble, forming a single phase with the water in the digestor and/or after fractionation. Or the solvent for lignin may form a separate phase from the water (or from a water-rich phase comprising the water) in the digestor and/or after fractionation (i.e. at reduced temperature compared to the digestor temperature).

The biomass feedstock may be selected from hardwoods, softwoods, forest residues, eucalyptus, industrial wastes, pulp and paper wastes, consumer wastes, or combinations thereof. Some embodiments utilize agricultural residues, which include lignocellulosic biomass associated with food crops, annual grasses, energy crops, or other annually renewable feedstocks. Exemplary agricultural residues include, but are not limited to, corn stover, corn fiber, wheat straw, sugarcane bagasse, sugarcane straw, rice straw, oat straw, barley straw, *miscanthus*, energy cane straw/residue, or combinations thereof. The process disclosed herein benefits from feedstock flexibility; it is effective for a wide variety of cellulose-containing feedstocks.

As used herein, "lignocellulosic biomass" means any material containing cellulose and lignin. Lignocellulosic biomass may also contain hemicellulose. Mixtures of one or more types of biomass can be used. In some embodiments, the biomass feedstock comprises both a lignocellulosic component (such as one described above) in addition to a sucrose-containing component (e.g., sugarcane or energy cane) and/or a starch component (e.g., corn, wheat, rice, etc.). Various moisture levels may be associated with the starting biomass. The biomass feedstock need not be, but may be, relatively dry. In general, the biomass is in the form of a particulate or chip, but particle size is not critical in this invention.

In some embodiments, during step (c), the cellulose-rich solids are treated with a total mechanical energy of less than about 5000 kilowatt-hours per ton of the cellulose-rich solids, less than about 2000 kilowatt-hours per ton of the cellulose-rich solids, or less than about 1000 kilowatt-hours per ton of the cellulose-rich solids.

In some embodiments, mechanical treating in step (c) further comprises treatment of the cellulose-rich solids with one or more acids, such as sulfur dioxide, sulfurous acid, lignosulfonic acid, acetic acid, formic acid, or combinations thereof. In some embodiments, mechanical treating in step (c) further comprises treatment of the cellulose-rich solids with one or more enzymes. In some embodiments, step (c) does not employ any enzymes or acids but optionally includes treatment of the cellulose-rich solids with heat.

The process further may include bleaching the cellulose-rich solids prior to step (c) and/or as part of step (c). The process alternatively or additionally may include bleaching the nanocellulose material during step (c) and/or following step (c).

The crystallinity of the nanocellulose material is at least 60%, in some embodiments.

In some preferred embodiments, the nanocellulose material is at least partially hydrophobic via deposition of at least some of the lignin onto a surface of the cellulose-rich solids during step (b). In these or other embodiments, the nanocellulose material is at least partially hydrophobic via deposition of at least some of the lignin onto a surface of the nanocellulose material during step (c) or step (d). Lignin that is not utilized in this way may later be recovered, combusted, or further treated.

The process of some embodiments further comprises hydrolyzing amorphous cellulose into glucose in step (b) and/or step (c), recovering the glucose, and optionally fermenting the glucose to a fermentation product. Optionally, the process further comprises recovering, fermenting, or further treating hemicellulosic sugars derived from the hemicellulose. In certain embodiments, the hemicellulosic sugars may be fermented (or chemically converted) to produce a monomer or precursor thereof; polymerizing the monomer to produce a polymer; and combining the polymer and the nanocellulose material to form a polymer-nanocellulose composite.

In some embodiments of the invention, the process further comprises chemically converting the nanocellulose material to one or more nanocellulose derivatives. Such nanocellulose derivatives may be selected from the group consisting of nanocellulose esters, nanocellulose ethers, nanocellulose ether esters, alkylated nanocellulose compounds, cross-linked nanocellulose compounds, acid-functionalized nanocellulose compounds, base-functionalized nanocellulose compounds, and combinations thereof.

Some variations provide a process for producing a hydrophobic nanocellulose material, the process comprising:
(a) providing a lignocellulosic biomass feedstock;
(b) fractionating the feedstock in the presence of a solvent for lignin and water, but no acid catalyst, to generate cellulose-rich solids and a liquid containing hemicellulose and lignin, wherein a portion of the lignin deposits onto a surface of the cellulose-rich solids, thereby rendering the cellulose-rich solids at least partially hydrophobic;
(c) mechanically treating the cellulose-rich solids to form a nanocellulose material comprising cellulose nanofibrils and/or cellulose nanocrystals; and
(d) recovering the hydrophobic nanocellulose material.

Some variations provide a process for producing a nanocellulose-containing product, the process comprising:
(a) providing a lignocellulosic biomass feedstock;
(b) fractionating the feedstock in the presence of a solvent for lignin and water, but no acid catalyst, to generate cellulose-rich solids and a liquid containing hemicellulose and lignin;
(c) mechanically treating the cellulose-rich solids to form a nanocellulose material comprising cellulose nanofibrils and/or cellulose nanocrystals; and
(d) incorporating at least a portion of the nanocellulose material into a nanocellulose-containing product.

In some embodiments, the nanocellulose material is at least partially hydrophobic via deposition of at least some of the lignin onto a surface of the cellulose-rich solids during step (b). The nanocellulose material may be made at least partially hydrophobic via deposition of at least some of the lignin onto a surface of the nanocellulose material during step (c) or step (d), i.e., after the digestor. A combination may be employed, in which some lignin is deposited onto (or into) cellulose fibers in the digestor, and then during or following mechanical treatment, more lignin is deposited onto (or into) the refined cellulose, to make hydrophobic nanocellulose.

In some embodiments, the nanocellulose-containing product consists essentially of the nanocellulose material. Many nanocellulose-containing products are possible. In some embodiments, step (d) comprises forming a structural object that includes the nanocellulose material, or a derivative thereof. In some embodiments, step (d) comprises forming a foam or aerogel that includes the nanocellulose material, or a derivative thereof. In some embodiments, step (d) comprises combining the nanocellulose material, or a derivative thereof, with one or more other materials to form a composite. The one or more other materials may include carbon or a polymer selected from polyolefins, polyesters, polyurethanes, polyamides, or combinations thereof, for example. In some embodiments, step (d) comprises forming a film comprising the nanocellulose material, or a derivative thereof. In some embodiments, wherein step (d) comprises forming a coating or coating precursor comprising the nanocellulose material, or a derivative thereof. In some embodiments, the nanocellulose-containing product is configured electrochemically for carrying or storing an electrical current or voltage. In some embodiments, the nanocellulose-containing product is incorporated into a filter, membrane, or other separation device. In some embodiments, the nanocellulose-containing product is incorporated as an additive into a coating, paint, or adhesive. In some embodiments, the nanocellulose-containing product is configured as a catalyst, catalyst substrate, or co-catalyst. In some embodiments, the nanocellulose-containing product is incorporated as a cement additive or concrete additive. In some embodiments, wherein the nanocellulose-containing product is a paper coating. In some embodiments, the nanocellulose-containing product is incorporated as a thickening agent or rheological modifier. In some embodiments, the nanocellulose-containing product is incorporated as an additive in a drilling fluid, a fracturing fluid, an oil recovery fluid, a gas recovery fluid, or combinations thereof.

Mechanically treating in step (c) may employ one or more known techniques such as, but by no means limited to, milling, grinding, beating, sonicating, or any other means to form or release nanofibrils and/or nanocrystals in the cellulose. Essentially, any type of mill or device that physically separates fibers may be utilized. Such mills are well-known in the industry and include, without limitation, Valley beaters, single disk refiners, double disk refiners, conical refiners, including both wide angle and narrow angle, cylindrical refiners, homogenizers, microfluidizers, and other similar milling or grinding apparatus. See, for example, Smook, *Handbook for Pulp & Paper Technologists*, Tappi Press, 1992; and Hubbe et al., "Cellulose Nanocomposites: A Review," *BioResources* 3(3), 929-980 (2008).

Mechanical comminution processing may be performed using conventional technologies known in the art, such as high shear forces, microfluidization, high-pressure homogenization, a high-pressure/high-shear homogenizer, controlled hydrodynamic cavitation, and high friction forces. Apparatus classified as a high-pressure or high-shear homogenizer, relies on the generation of high mechanical stresses within the fluid to achieve breakdown of the cellulosic feedstock into the desired nanocellulose. This is achieved by pumping the fluid formulation through a well-defined microfluidic interaction chamber.

The extent of mechanical treatment may be monitored during the process by any of several means. Certain optical instruments can provide continuous data relating to the fiber length distributions and % fines, either of which may be used to define endpoints for the mechanical treatment step. The time, temperature, and pressure may vary during mechanical treatment. For example, in some embodiments, sonication for a time from about 5 minutes to 2 hours, at ambient temperature and pressure, may be utilized.

In some embodiments, during step (c), the cellulose-rich solids are treated with a total mechanical energy of less than about 5000 kilowatt-hours per ton of the cellulose-rich solids, such as less than about 4500, 4000, 3500, 3000, 2500, 2000, 1500, 1000, or 500 kilowatt-hours per ton of the cellulose-rich solids. Energy consumption may be measured in any other suitable units. An ammeter measuring current drawn by a motor driving the mechanical treatment device is one way to obtain an estimate of the total mechanical energy.

Note that in some embodiments, the mechanical energy is determined or estimated in a laboratory procedure, as a way to characterize the precursor pulp that is produced by solvent fractionation. The specific mechanical energy (kilowatt-hours per ton) does not necessarily translate to large-scale commercial equipment, even if the principles of the processing remain the same. As a specific example, after fractionation, the cellulose-rich solids may be converted to nanocellulose in a laboratory an using an M110-EH Microfluidizer (Microfluidics Corp.) fitted with two chambers in series. The first chamber is the auxiliary processing module (APM) and comprises a ceramic module with a 200-micron diameter channel and the second is called the interaction chamber (IXC) and has a diamond channel with a 100-micron diameter channel. The mechanical refining energy estimated in this procedure may less than about 5000 kilowatt-hours per ton of the cellulose-rich solids, such as less than about 4500, 4000, 3500, 3000, 2500, 2000, 1500, 1000, or 500 kilowatt-hours per ton of the cellulose-rich solids. The mechanical refining energy at commercial scale may be lower or higher than at the lab scale, depending on the specific equipment and configuration.

In some embodiments, a portion of the cellulose-rich solids is converted to nanofibrils while the remainder of the cellulose-rich solids is not fibrillated. In various embodiments, about 10%, 20%, 30%, 40%, 50%, 60%, 70%, 80%, 90%, 95%, 99%, or substantially all of the cellulose-rich solids are fibrillated into nanofibrils.

In some embodiments, a portion of the nanofibrils is converted to nanocrystals while the remainder of the nanofibrils is not converted to nanocrystals. In various embodiments, about 10%, 20%, 30%, 40%, 50%, 60%, 70%, 80%, 90%, 95%, 99%, or substantially all of the nanofibrils are converted to nanocrystals. During drying, it is possible for a small amount of nanocrystals to come back together and form nanofibrils.

Following mechanical treatment, the nanocellulose material may be classified by particle size. A portion of material may be subjected to a separate process, such as enzymatic hydrolysis to produce glucose. Such material may have good crystallinity, for example, but may not have desirable particle size or degree of polymerization.

Step (c) may further comprise treatment of the cellulose-rich solids with one or more enzymes or with one or more acids. When acids are employed, they may be selected from the group consisting of sulfur dioxide, sulfurous acid, lignosulfonic acid, acetic acid, formic acid, and combinations thereof. Acids associated with hemicellulose, such as acetic acid or uronic acids, may be employed, alone or in conjunction with other acids. Also, step (c) may include treatment of the cellulose-rich solids with heat. In some embodiments, step (c) does not employ any enzymes or acids.

In step (c), when an acid is employed, the acid may be a strong acid such as sulfuric acid, nitric acid, or phosphoric acid, for example. Weaker acids may be employed, under more severe temperature and/or time. Enzymes that hydrolyze cellulose (i.e., cellulases) and possibly hemicellulose (i.e., with hemicellulase activity) may be employed in step (c), either instead of acids, or potentially in a sequential configuration before or after acidic hydrolysis.

In some embodiments, the process comprises enzymatically treating the cellulose-rich solids to hydrolyze amorphous cellulose. In other embodiments, or sequentially prior to or after enzymatic treatment, the process may comprise acid-treating the cellulose-rich solids to hydrolyze amorphous cellulose.

In some embodiments, the process further comprises enzymatically treating the nanocrystalline cellulose. In other embodiments, or sequentially prior to or after enzymatic treatment, the process further comprises acid-treating treating the nanocrystalline cellulose.

If desired, an enzymatic treatment may be employed prior to, or possibly simultaneously with, the mechanical treatment. However, in preferred embodiments, no enzyme treatment is necessary to hydrolyze amorphous cellulose or weaken the structure of the fiber walls before isolation of nanofibers.

Following mechanical treatment, the nanocellulose may be recovered. Separation of cellulose nanofibrils and/or nanocrystals may be accomplished using apparatus capable of disintegrating the ultrastructure of the cell wall while preserving the integrity of the nanofibrils. For example, a homogenizer may be employed. In some embodiments, cellulose aggregate fibrils are recovered, having component fibrils in range of 1-100 nm width, wherein the fibrils have not been completely separated from each other.

The process may further comprise bleaching the cellulose-rich solids prior to step (c) and/or as part of step (c). Alternatively, or additionally, the process may further comprise bleaching the nanocellulose material during step (c) and/or following step (c). Any known bleaching technology or sequence may be employed, including enzymatic bleaching.

The nanocellulose material may include, or consist essentially of, nanofibrillated cellulose. The nanocellulose material may include, or consist essentially of, nanocrystalline cellulose. In some embodiments, the nanocellulose material may include, or consist essentially of, nanofibrillated cellulose and nanocrystalline cellulose.

In some embodiments, the crystallinity of the cellulose-rich solids (i.e., the nanocellulose precursor material) is at least 60%, 61%, 62%, 63%, 64%, 65%, 66%, 67%, 68%, 69%, 70%, 71%, 72%, 73%, 74%, 75%, 76%, 77%, 78%, 79%, 80%, or higher. In these or other embodiments, the crystallinity of the nanocellulose material is at least 60%, 61%, 62%, 63%, 64%, 65%, 66%, 67%, 68%, 69%, 70%, 71%, 72%, 73%, 74%, 75%, 76%, 77%, 78%, 79%, 80%, or higher. The crystallinity may be measured using any known techniques. For example, X-ray diffraction and solid-state $^{13}C$ nuclear magnetic resonance may be utilized.

In some embodiments, the nanocellulose material is characterized by an average degree of polymerization from about 100 to about 1500, such as about 125, 150, 175, 200, 225, 250, 300, 400, 500, 600, 700, 800, 900, 1000, 1100, 1200, 1300, or 1400. For example, the nanocellulose material may be characterized by an average degree of polymerization from about 300 to about 700, or from about 150 to about 250. The nanocellulose material, when in the form of nanocrystals, may have a degree of polymerization less than 100, such as about 75, 50, 25, or 10. Portions of the material may have a degree of polymerization that is higher than 1500, such as about 2000, 3000, 4000, or 5000.

In some embodiments, the nanocellulose material is characterized by a degree of polymerization distribution having a single peak. In other embodiments, the nanocellulose material is characterized by a degree of polymerization distribution having two peaks, such as one centered in the range of 150-250 and another peak centered in the range of 300-700.

In some embodiments, the nanocellulose material is characterized by an average length-to-width aspect ratio of particles from about 10 to about 1000, such as about 15, 20, 25, 35, 50, 75, 100, 150, 200, 250, 300, 400, or 500. Nanofibrils are generally associated with higher aspect ratios than nanocrystals. Nanocrystals, for example, may have a length range of about 100 nm to 500 nm and a diameter of about 4 nm, translating to an aspect ratio of 25 to 125. Nanofibrils may have a length of about 2000 nm and diameter range of 5 to 50 nm, translating to an aspect ratio of 40 to 400. In some embodiments, the aspect ratio is less than 50, less than 45, less than 40, less than 35, less than 30, less than 25, less than 20, less than 15, or less than 10.

Optionally, the process further comprises hydrolyzing amorphous cellulose into glucose in step (b) and/or step (c), recovering the glucose, and fermenting the glucose to a fermentation product. Optionally, the process further comprises recovering, fermenting, or further treating hemicellulosic sugars derived from the hemicellulose. Optionally, the process further comprises recovering, combusting, or further treating the lignin.

Glucose that is generated from hydrolysis of amorphous cellulose may be integrated into an overall process to produce ethanol, or another fermentation co-product. Thus in some embodiments, the process further comprises hydrolyzing amorphous cellulose into glucose in step (b) and/or step (c), and recovering the glucose. The glucose may be purified and sold. Or the glucose may be fermented to a fermentation product, such as but not limited to ethanol. The glucose or a fermentation product may be recycled to the front end, such as to hemicellulose sugar processing, if desired.

When hemicellulosic sugars are recovered and fermented, they may be fermented to produce a monomer or precursor thereof. The monomer may be polymerized to produce a polymer, which may then be combined with the nanocellulose material to form a polymer-nanocellulose composite.

In some embodiments, the nanocellulose material is at least partially hydrophobic via deposition of at least some of the lignin onto a surface of the cellulose-rich solids during step (b). The choice of solvent will impact both the initial delignification chemistry as well as the precipitation (redeposition) of the lignin back onto the cellulose fibers, all of which also depends on temperature, time, pH, and can depend on feedstock type. In these or other embodiments, the nanocellulose material is at least partially hydrophobic via deposition of at least some of the lignin onto a surface of the nanocellulose material during step (c) or step (d).

In some embodiments, the process further comprises chemically converting the nanocellulose material to one or more nanocellulose derivatives. For example, nanocellulose derivatives may be selected from the group consisting of nanocellulose esters, nanocellulose ethers, nanocellulose ether esters, alkylated nanocellulose compounds, crosslinked nanocellulose compounds, acid-functionalized nanocellulose compounds, base-functionalized nanocellulose compounds, and combinations thereof.

Various types of nanocellulose functionalization or derivatization may be employed, such as functionalization using polymers, chemical surface modification, functionalization using nanoparticles (i.e. other nanoparticles besides the nanocellulose), modification with inorganics or surfactants, or biochemical modification.

A significant factor limiting the application of strength-enhancing, lightweight nanocellulose in composites is cellulose's inherent hydrophilicity. Surface modification of the nanocellulose surface to impart hydrophobicity to enable uniform dispersion in a hydrophobic polymer matrix is an active area of study. It has been discovered that when preparing nanocellulose using the processes described herein, lignin may condense on pulp under certain conditions, giving a rise in Kappa number and production of a brown or black material. The lignin increases the hydrophobicity of the nanocellulose precursor material, and that hydrophobicity is retained during mechanical treatment provided that there is not removal of the lignin through bleaching or other steps. (Some bleaching may still be performed, either to adjust lignin content or to attack a certain type of lignin, for example.)

In some embodiments, the present invention provides a process for producing a hydrophobic nanocellulose material, the process comprising:

(a) providing a lignocellulosic biomass feedstock;
(b) fractionating the feedstock in the presence of a solvent for lignin and water, to generate cellulose-rich solids and a liquid containing hemicellulose and lignin, wherein a portion of the lignin deposits onto a surface of the cellulose-rich solids, thereby rendering the cellulose-rich solids at least partially hydrophobic;
(c) mechanically treating the cellulose-rich solids to form a hydrophobic nanocellulose material containing hydrophobic cellulose nanofibrils and/or hydrophobic nanocellulose crystals; and
(d) recovering the hydrophobic nanocellulose material.

In some embodiments, during step (c), the cellulose-rich solids are treated with a total mechanical energy of less than about 2000 kilowatt-hours per ton of the cellulose-rich solids, such as less than about 1000 kilowatt-hours per ton of the cellulose-rich solids.

The crystallinity of the nanocellulose material is at least 70% or at least 80%, in various embodiments.

The nanocellulose material may include nanofibrillated cellulose, nanocrystalline cellulose, or both nanofibrillated and nanocrystalline cellulose. The nanocellulose material may be characterized by an average degree of polymerization from about 100 to about 1500, such as from about 300 to about 700, or from about 150 to about 250, for example (without limitation).

Step (b) may include process conditions, such as extended time and/or temperature, or reduced concentration of solvent for lignin, which tend to promote lignin deposition onto fibers. Alternatively, or additionally, step (b) may include one or more washing steps that are adapted to deposit at least some of the lignin that was solubilized during the initial fractionation. One approach is to wash with water rather than a solution of water and solvent. Because lignin is generally not soluble in water, it will begin to precipitate. Optionally, other conditions may be varied, such as pH and temperature, during fractionation, washing, or other steps, to optimize the amount of lignin deposited on surfaces. It is noted that in order for the lignin surface concentration to be higher than the bulk concentration, the lignin needs to be first pulled into solution and then redeposited.

Optionally, the process for producing a hydrophobic nanocellulose material may further include chemically modifying the lignin to increase hydrophobicity of the nanocellulose material. The chemical modification of lignin may be conducted during step (b), step (c), step (d), following step (d), or some combination.

High loading rates of lignin have been achieved in thermoplastics. Even higher loading levels are obtained with well-known modifications of lignin. The preparation of useful polymeric materials containing a substantial amount of lignin has been the subject of investigations for more than thirty years. Typically, lignin may be blended into polyolefins or polyesters by extrusion up to 25-40 wt % while satisfying mechanical characteristics. In order to increase the compatibility between lignin and other hydrophobic polymers, different approaches have been used. For example, chemical modification of lignin may be accomplished through esterification with long-chain fatty acids.

Any known chemical modifications may be carried out on the lignin, to further increase the hydrophobic nature of the lignin-coated nanocellulose material provided by embodiments of this invention.

Nanocellulose-containing products includes the nanocellulose material, or a treated form thereof. In some embodiments, the nanocellulose-containing product consists essentially of the nanocellulose material.

In some embodiments, step (d) comprises forming a structural object that includes the nanocellulose material, or a derivative thereof.

In some embodiments, step (d) comprises forming a foam or aerogel that includes the nanocellulose material, or a derivative thereof.

In some embodiments, step (d) comprises combining the nanocellulose material, or a derivative thereof, with one or more other materials to form a composite. For example, the other material may include a polymer selected from polyolefins, polyesters, polyurethanes, polyamides, or combinations thereof. Alternatively, or additionally, the other material may include carbon in various forms.

The nanocellulose material incorporated into a nanocellulose-containing product may be at least partially hydrophobic via deposition of at least some of the lignin onto a surface of the cellulose-rich solids during step (b). Also, the nanocellulose material may be at least partially hydrophobic via deposition of at least some of the lignin onto a surface of the nanocellulose material during step (c) or step (d).

In some embodiments, step (d) comprises forming a film comprising the nanocellulose material, or a derivative thereof. The film is optically transparent and flexible, in certain embodiments.

In some embodiments, step (d) comprises forming a coating or coating precursor comprising the nanocellulose material, or a derivative thereof. In some embodiments, the nanocellulose-containing product is a paper coating.

In some embodiments, the nanocellulose-containing product is configured as a catalyst, catalyst substrate, or co-catalyst. In some embodiments, the nanocellulose-containing product is configured electrochemically for carrying or storing an electrical current or voltage.

In some embodiments, the nanocellulose-containing product is incorporated into a filter, membrane, or other separation device.

In some embodiments, the nanocellulose-containing product is incorporated as an additive into a coating, paint, or adhesive. In some embodiments, the nanocellulose-containing product is incorporated as a cement additive.

In some embodiments, the nanocellulose-containing product is incorporated as a thickening agent or rheological modifier. For example, the nanocellulose-containing product may be an additive in a drilling fluid, such as (but not limited to) an oil recovery fluid and/or a gas recovery fluid.

The present invention also provides nanocellulose compositions. In some variations, a nanocellulose composition comprises nanofibrillated cellulose with a cellulose crystallinity of about 70% or greater.

In some variations, a nanocellulose composition comprises nanofibrillated cellulose and nanocrystalline cellulose, wherein the nanocellulose composition is characterized by an overall cellulose crystallinity of about 70% or greater. The nanocellulose composition may include lignin. The nanocellulose composition may include an amount of residual solvent (such as 0.01 wt %, 0.05 wt %, 0.1 wt %, 0.2 wt %, or more) that provides some benefit in certain applications, such as to function as a plasticizer in polymer composites.

In some embodiments, the cellulose crystallinity is about 75% or greater, such as about 80% or greater, or about 85% or greater. In various embodiments, the nanocellulose composition is not derived from tunicates.

The nanocellulose composition of some embodiments is characterized by an average cellulose degree of polymerization from about 100 to about 1000, such as from about 300 to about 700 or from about 150 to about 250. In certain embodiments, the nanocellulose composition is characterized by a cellulose degree of polymerization distribution having a single peak. In certain embodiments, the nanocellulose composition is free of enzymes.

Other variations provide a hydrophobic nanocellulose composition with a cellulose crystallinity of about 70% or greater, wherein the nanocellulose composition contains nanocellulose particles having a surface concentration of lignin that is greater than a bulk (internal particle) concentration of lignin. In some embodiments, there is a coating or thin film of lignin on nanocellulose particles, but the coating or film need not be uniform.

The hydrophobic nanocellulose composition is preferably not derived from tunicates or bacterial cellulose. The hydrophobic nanocellulose composition may be free of enzymes.

In some embodiments, the hydrophobic nanocellulose composition is characterized by an average cellulose degree of polymerization from about 100 to about 1500, such as from about 300 to about 700 or from about 150 to about 250. The nanocellulose composition may be characterized by a cellulose degree of polymerization distribution having a single peak.

A nanocellulose-containing product may include any of the disclosed nanocellulose compositions. Many nanocellulose-containing products are possible. For example, a nanocellulose-containing product may be selected from the group consisting of a structural object, a foam, an aerogel, a polymer composite, a carbon composite, a film, a coating, a coating precursor, a current or voltage carrier, a filter, a membrane, a catalyst, a catalyst substrate, a coating additive, a paint additive, an adhesive additive, a cement additive, a paper coating, a thickening agent, a rheological modifier, an additive for a drilling fluid, and combinations or derivatives thereof.

Preferably, enough solvent is included in the extractant mixture to dissolve the lignin present in the starting material. The solvent for lignin may be completely miscible, partially miscible, or immiscible with water, so that there may be more than one liquid phase. Potential process advantages arise when the solvent is miscible with water, and also when the solvent is immiscible with water. When the solvent is water-miscible, a single liquid phase forms, so mass transfer of lignin and hemicellulose extraction is enhanced, and the downstream process must only deal with one liquid stream. When the solvent is immiscible in water, the extractant mixture readily separates to form liquid phases, so a distinct separation step can be avoided or simplified. This can be advantageous if one liquid phase contains most of the lignin and the other contains most of the hemicellulose sugars, as this facilitates recovering the lignin from the hemicellulose sugars.

The pH of the cooking liquor is typically about 2 to 5. In various embodiments, the pH of the cooking liquor (measured following fractionation) is from about 2 to about 12, such as about 3 to about 10, or about 4 to about 8. The pH of the cooking liquor will depend on the choice of solvent(s), the concentration of solvent(s), and the nature of the feedstock (e.g., ash and buffering capacity of the feedstock). During the fractionation, acids may be generated, such as acetic acid from released acetyl groups (from the biomass), possible sugar degradation at high temperature, etc. Optionally, the pH may be adjusted with an acid or a base, to a desired pH value or range.

In some embodiments, an additive may be included in amounts of about 0.1 wt % to 10 wt % or more to increase cellulose viscosity. Exemplary additives include ammonia, ammonia hydroxide, urea, anthraquinone, magnesium oxide, magnesium hydroxide, sodium hydroxide, and their derivatives.

The cooking is performed in one or more stages using batch or continuous digestors. Solid and liquid may flow cocurrently or countercurrently, or in any other flow pattern that achieves the desired fractionation. The cooking reactor may be internally agitated, if desired.

Depending on the lignocellulosic material to be processed, the cooking conditions are varied, with temperatures from about 100° C. to 220° C., for example 105° C., 115° C., 125° C., 130° C., 135° C., 140° C., 145° C., 150° C., 155° C., 165° C., 170° C., 175° C., 180° C., 185° C., 190° C., 195° C., 200° C., 205° C., 210° C., or 215° C., and corresponding pressures from about 1 atmosphere to about 20 atmospheres in the liquid or vapor phase. The cooking time of one or more stages may be selected from about 15 minutes to about 720 minutes, such as about 30, 45, 60, 90, 120, 140, 160, 180, 250, 300, 360, 450, 550, 600, or 700 minutes. Generally, there is an inverse relationship between the temperature used during the digestion step and the time needed to obtain good fractionation of the biomass into its constituent parts.

The cooking liquor to lignocellulosic material ratio may be selected from about 1 to about 10, such as about 2, 3, 4, 5, or 6. In some embodiments, biomass is digested in a pressurized vessel with low liquor volume (low ratio of cooking liquor to lignocellulosic material), so that the cooking space is filled with solvent vapor in equilibrium with moisture. The cooked biomass is washed in alcohol-rich solution to recover lignin and dissolved hemicelluloses, while the remaining pulp is further processed.

Once the desired amount of fractionation of both hemicellulose and lignin from the solid phase is achieved, the liquid and solid phases are separated. Conditions for the separation may be selected to minimize or enhance the reprecipitation of the extracted lignin on the solid phase. Minimizing lignin reprecipitation is favored by conducting separation or washing at a temperature of at least the glass-transition temperature of lignin (about 120° C.); conversely, enhancing lignin reprecipitation is favored by conducting separation or washing at a temperature less than the glass-transition temperature of lignin.

The physical separation can be accomplished either by transferring the entire mixture to a device that can carry out the separation and washing, or by removing only one of the phases from the reactor while keeping the other phase in place. The solid phase can be physically retained by appropriately sized screens through which liquid can pass. The solid is retained on the screens and can be kept there for successive solid-wash cycles. Alternately, the liquid may be retained and solid phase forced out of the reaction zone, with centrifugal or other forces that can effectively transfer the solids out of the slurry. In a continuous system, countercurrent flow of solids and liquid can accomplish the physical separation.

The recovered solids normally will contain a quantity of lignin and sugars, some of which can be removed easily by washing. The washing-liquid composition can be the same as or different than the liquor composition used during fractionation. Multiple washes may be performed to increase effectiveness. Preferably, one or more washes are performed with a composition including a solvent for lignin, to remove additional lignin from the solids, followed by one or more washes with water to displace residual solvent and sugars from the solids. Recycle streams, such as from solvent-recovery operations, may be used to wash the solids.

After separation and washing as described, a solid phase and at least one liquid phase are obtained. The solid phase contains substantially undigested cellulose. A single liquid phase is usually obtained when the solvent and the water are miscible in the relative proportions that are present. In that case, the liquid phase contains, in dissolved form, most of the lignin originally in the starting lignocellulosic material, as well as soluble monomeric and oligomeric sugars formed in the hydrolysis of any hemicellulose that may have been present. Multiple liquid phases tend to form when the solvent and water are wholly or partially immiscible. The lignin tends to be contained in the liquid phase that contains most of the solvent. Hemicellulose hydrolysis products tend to be present in the liquid phase that contains most of the water.

In some embodiments, hydrolysate from the cooking step is subjected to pressure reduction. Pressure reduction may be done at the end of a cook in a batch digestor, or in an external flash tank after extraction from a continuous digestor, for example. The flash vapor from the pressure reduction may be collected into a cooking liquor make-up vessel. The cellulose is then removed to be washed and further treated as desired.

A process washing step recovers the hydrolysate from the cellulose. The washed cellulose is pulp that may be used for various purposes (e.g., paper or nanocellulose production). The weak hydrolysate from the washer continues to the final reaction step; in a continuous digestor this weak hydrolysate may be combined with the extracted hydrolysate from the external flash tank. In some embodiments, washing and/or separation of hydrolysate and cellulose-rich solids is conducted at a temperature of at least about 100° C., 110° C., or 120° C. The washed cellulose may also be used for glucose production via cellulose hydrolysis with enzymes or acids.

In another reaction step, the hydrolysate may be further treated in one or multiple steps to hydrolyze the oligomers into monomers. This step may be conducted before, during, or after the removal of solvent. The solution may or may not contain residual solvent (e.g. alcohol). In some embodiments, sulfur dioxide is added to this step, to assist hydrolysis. In these or other embodiments, an acid such as sulfurous acid or sulfuric acid is introduced to assist with hydrolysis. In some embodiments, the hydrolysate is autohydrolyzed by heating under pressure. In various embodiments, this step utilizes sulfur dioxide, sulfurous acid, or sulfuric acid at a concentration of about 0.01 wt % to 30 wt %, such as about 0.05 wt %, 0.1 wt %, 0.2 wt %, 0.5 wt %, 1 wt %, 2 wt %, 5 wt %, 10 wt %, or 20 wt %. This step may be carried out at a temperature from about 100° C. to 220° C., such as about 110° C., 120° C., 130° C., 140° C., 150° C., 160° C., 170° C., 180° C., 190° C., 200° C., or 210° C. Heating may be direct or indirect to reach the selected temperature.

The reaction step produces fermentable sugars which can then be concentrated by evaporation to a fermentation feedstock. Concentration by evaporation may be accomplished before, during, or after the treatment to hydrolyze oligomers. The final reaction step may optionally be followed by steam stripping of the resulting hydrolysate to remove potential fermentation-inhibiting side products. The evaporation process may be under vacuum or pressure, from about −0.1 atmospheres to about 10 atmospheres, such as about 0.1 atm, 0.3 atm, 0.5 atm, 1.0 atm, 1.5 atm, 2 atm, 4 atm, 6 atm, or 8 atm.

In a preferred embodiment, the evaporation step utilizes an integrated solventy stripper and evaporator. Evaporated vapor streams may be segregated so as to have different concentrations of organic compounds in different streams. Evaporator condensate streams may be segregated so as to have different concentrations of organic compounds in different streams. Alcohol may be recovered from the evaporation process by condensing the exhaust vapor and returning to the cooking liquor make-up vessel in the cooking step. Clean condensate from the evaporation process may be used in the washing step.

In some embodiments, an integrated alcohol stripper and evaporator system is employed, wherein aliphatic alcohol is removed by vapor stripping, the resulting stripper product stream is concentrated by evaporating water from the stream, and evaporated vapor is compressed using vapor compression and is reused to provide thermal energy.

The hydrolysate from the evaporation and final reaction step contains mainly fermentable sugars but may also contain lignin depending on the location of lignin separation in the overall process configuration. The hydrolysate may be concentrated to a concentration of about 5 wt % to about 60 wt % solids, such as about 10 wt %, 15 wt %, 20 wt %, 25 wt %, 30 wt %, 35 wt %, 40 wt %, 45 wt %, 50 wt % or 55 wt % solids. The hydrolysate contains fermentable sugars.

Fermentable sugars are defined as hydrolysis products of cellulose, galactoglucomannan, glucomannan, arabinoglucuronoxylans, arabinogalactan, and glucuronoxylans into their respective short-chained oligomers and monomer products, i.e., glucose, mannose, galactose, xylose, and arabinose. The fermentable sugars may be recovered in purified form, as a sugar slurry or dry sugar solids, for example. Any known technique may be employed to recover a slurry of sugars or to dry the solution to produce dry sugar solids.

In some embodiments, the fermentable sugars are fermented to produce biochemicals or biofuels such as (but by no means limited to) ethanol, isopropanol, acetone, 1-butanol, isobutanol, lactic acid, succinic acid, or any other fermentation products. Some amount of the fermentation product may be a microorganism or enzymes, which may be recovered if desired.

The process lignin separation step is for the separation of lignin from the hydrolysate and can be located before or after the final reaction step and evaporation. If located after, then lignin will precipitate from the hydrolysate since alcohol has been removed in the evaporation step. Native (non-sulfonated) lignin is hydrophobic. In some embodiments, the process further comprises recovering the lignin as a co-product.

The process fermentation and distillation steps are intended for the production of fermentation products, such as alcohols or organic acids. After removal of cooking chemicals and lignin, and further treatment (oligomer hydrolysis), the hydrolysate contains mainly fermentable sugars in water solution from which any fermentation inhibitors have been preferably removed or neutralized. The hydrolysate is fermented to produce dilute alcohol or organic acids, from 1 wt % to 20 wt % concentration. The dilute product is distilled or otherwise purified as is known in the art.

When alcohol is produced, such as ethanol, some of it may be used for cooking liquor makeup in the process cooking step. Also, in some embodiments, a distillation column stream, such as the bottoms, with or without evaporator condensate, may be reused to wash cellulose. In some embodiments, lime may be used to dehydrate product alcohol. Side products may be removed and recovered from the hydrolysate. These side products may be isolated by processing the vent from the final reaction step and/or the condensate from the evaporation step. Side products include furfural, hydroxymethyl furfural (HMF), methanol, acetic acid, and lignin-derived compounds, for example.

The glucose may be fermented to an alcohol, an organic acid, or another fermentation product. The glucose may be used as a sweetener or isomerized to enrich its fructose content. The glucose may be used to produce baker's yeast. The glucose may be catalytically or thermally converted to various organic acids and other materials.

When hemicellulose is present in the starting biomass, all or a portion of the liquid phase contains hemicellulose sugars and soluble oligomers. It is preferred to remove most of the lignin from the liquid, as described above, to produce a fermentation broth which will contain water, possibly some of the solvent for lignin, hemicellulose sugars, and various minor components from the digestion process. This fermentation broth can be used directly, combined with one or more other fermentation streams, or further treated. Further treatment can include sugar concentration by evaporation; addition of glucose or other sugars (optionally as obtained from cellulose saccharification); addition of various nutrients such as salts, vitamins, or trace elements; pH adjustment; and removal of fermentation inhibitors such as acetic acid and phenolic compounds. The choice of conditioning steps should be specific to the target product(s) and microorganism(s) employed.

In some embodiments, hemicellulose sugars are not fermented but rather are recovered and purified, stored, sold, or converted to a specialty product. Xylose, for example, can be converted into xylitol.

A lignin product can be readily obtained from a liquid phase using one or more of several methods. One simple technique is to evaporate off all liquid, resulting in a solid lignin-rich residue. This technique would be especially advantageous if the solvent for lignin is water-immiscible. Another method is to cause the lignin to precipitate out of solution. Some of the ways to precipitate the lignin include (1) removing the solvent for lignin from the liquid phase, but not the water, such as by selectively evaporating the solvent from the liquid phase until the lignin is no longer soluble; (2) diluting the liquid phase with water until the lignin is no longer soluble; and (3) adjusting the temperature and/or pH of the liquid phase. Methods such as centrifugation can then be utilized to capture the lignin. Yet another technique for removing the lignin is continuous liquid-liquid extraction to selectively remove the lignin from the liquid phase, followed by removal of the extraction solvent to recover relatively pure lignin.

Lignin produced in accordance with the invention can be used as a fuel. As a solid fuel, lignin is similar in energy content to coal. Lignin can act as an oxygenated component in liquid fuels, to enhance octane while meeting standards as a renewable fuel. The lignin produced herein can also be used as polymeric material, and as a chemical precursor for producing lignin derivatives.

The present invention also provides systems configured for carrying out the disclosed processes, and compositions produced therefrom. Any stream generated by the disclosed processes may be partially or completed recovered, purified or further treated, and/or marketed or sold.

Certain nanocellulose-containing products provide high transparency, good mechanical strength, and/or enhanced gas (e.g., $O_2$ or $CO_2$) barrier properties, for example. Certain nanocellulose-containing products containing hydrophobic nanocellulose materials provided herein may be useful as anti-wetting and anti-icing coatings, for example.

Due to the low mechanical energy input, nanocellulose-containing products provided herein may be characterized by fewer defects that normally result from intense mechanical treatment.

Some embodiments provide nanocellulose-containing products with applications for sensors, catalysts, antimicrobial materials, current carrying and energy storage capabilities. Cellulose nanocrystals have the capacity to assist in the synthesis of metallic and semiconducting nanoparticle chains.

Some embodiments provide composites containing nanocellulose and a carbon-containing material, such as (but not limited to) lignin, graphite, graphene, or carbon aerogels.

Cellulose nanocrystals may be coupled with the stabilizing properties of surfactants and exploited for the fabrication of nanoarchitectures of various semiconducting materials.

The reactive surface of —OH side groups in nanocellulose facilitates grafting chemical species to achieve different surface properties. Surface functionalization allows the tailoring of particle surface chemistry to facilitate self-assembly, controlled dispersion within a wide range of matrix polymers, and control of both the particle-particle and particle-matrix bond strength. Composites may be transparent, have tensile strengths greater than cast iron, and have very low coefficient of thermal expansion. Potential applications include, but are not limited to, barrier films, antimicrobial films, transparent films, flexible displays, reinforcing fillers for polymers, biomedical implants, pharmaceuticals, drug delivery, fibers and textiles, templates for electronic components, separation membranes, batteries, supercapacitors, electroactive polymers, and many others.

Other nanocellulose applications suitable to the present invention include reinforced polymers, high-strength spun fibers and textiles, advanced composite materials, films for barrier and other properties, additives for coatings, paints, lacquers and adhesives, switchable optical devices, pharmaceuticals and drug delivery systems, bone replacement and tooth repair, improved paper, packaging and building products, additives for foods and cosmetics, catalysts, and hydrogels.

Aerospace and transportation composites may benefit from high crystallinity. Automotive applications include nanocellulose composites with polypropylene, polyamide (e.g. Nylons), or polyesters (e.g. PBT).

Nanocellulose materials provided herein are suitable as strength-enhancing additives for renewable and biodegradable composites. The cellulosic nanofibrillar structures may function as a binder between two organic phases for improved fracture toughness and prevention of crack formation for application in packaging, construction materials, appliances, and renewable fibers.

Nanocellulose materials provided herein are suitable as transparent and dimensional stable strength-enhancing additives and substrates for application in flexible displays, flexible circuits, printable electronics, and flexible solar panels. Nanocellulose is incorporated into the substrate-sheets are formed by vacuum filtration, dried under pressure and calandered, for example. In a sheet structure, nanocellulose acts as a glue between the filler aggregates. The formed calandered sheets are smooth and flexible.

Nanocellulose materials provided herein are suitable for composite and cement additives allowing for crack reduction and increased toughness and strength. Foamed, cellular nanocellulose-concrete hybrid materials allow for lightweight structures with increased crack reduction and strength.

Strength enhancement with nanocellulose increases both the binding area and binding strength for application in high strength, high bulk, high filler content paper and board with enhanced moisture and oxygen barrier properties. The pulp and paper industry in particular may benefit from nanocellulose materials provided herein.

Nanofibrillated cellulose nanopaper has a higher density and higher tensile mechanical properties than conventional paper. It can also be optically transparent and flexible, with low thermal expansion and excellent oxygen barrier characteristics. The functionality of the nanopaper can be further broadened by incorporating other entities such as carbon nanotubes, nanoclay or a conductive polymer coating.

Porous nanocellulose may be used for cellular bioplastics, insulation and plastics and bioactive membranes and filters. Highly porous nanocellulose materials are generally of high interest in the manufacturing of filtration media as well as for biomedical applications, e.g., in dialysis membranes.

Nanocellulose materials provided herein are suitable as coating materials as they are expected to have a high oxygen barrier and affinity to wood fibers for application in food packaging and printing papers.

Nanocellulose materials provided herein are suitable as additives to improve the durability of paint, protecting paints and varnishes from attrition caused by UV radiation.

Nanocellulose materials provided herein are suitable as thickening agents in food and cosmetics products. Nanocellulose can be used as thixotropic, biodegradable, dimensionally stable thickener (stable against temperature and salt addition). Nanocellulose materials provided herein are suitable as a Pickering stabilizer for emulsions and particle stabilized foam.

The large surface area of these nanocellulose materials in combination with their biodegradability makes them attractive materials for highly porous, mechanically stable aerogels. Nanocellulose aerogels display a porosity of 95% or higher, and they are ductile and flexible.

Drilling fluids are fluids used in drilling in the natural gas and oil industries, as well as other industries that use large drilling equipment. The drilling fluids are used to lubricate, provide hydrostatic pressure, and to keep the drill cool, and the hole as clean as possible of drill cuttings. Nanocellulose materials provided herein are suitable as additives to these drilling fluids as well as fracturing fluid.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

All publications, patents, and patent applications cited in this specification are herein incorporated by reference in their entirety as if each publication, patent, or patent application were specifically and individually put forth herein.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing a nanocellulose material, said process comprising:
    (a) providing a lignocellulosic biomass feedstock;
    (b) chemically fractionating said feedstock at a fractionation temperature selected from 110° C. to 220° C., a fractionation pressure selected from 1 atm to 20 atm, and a fractionation time selected from 15 minutes to 720 minutes, in the presence of a solution consisting of a solvent for lignin and water, to generate a solid phase of cellulose-rich solids and a liquid containing hemicellulose and lignin, wherein said solvent for lignin is selected from the group consisting of oxygenated organic compounds, aliphatic alcohols, aromatic alcohols, ketones, aldehydes, ethers, non-oxygenated alkanes, non-oxygenated olefins, non-oxygenated aromatic hydrocarbons, ionic liquids, and combinations thereof, wherein step (b) does not include introducing an acid, and wherein said solvent for lignin is not an acid catalyst;
    (c) following step (b), physically separating said cellulose-rich solids from said liquid, thereby generating separated cellulose-rich solids;
    (d) following step (c), mechanically treating said separated cellulose-rich solids to form a nanocellulose material comprising cellulose nanofibrils and/or cellulose nanocrystals, and
    (e) recovering said nanocellulose material.

2. The process of claim 1, wherein said solvent for lignin is an oxygenated organic compound.

3. The process of claim 2, wherein said solvent for lignin is an aliphatic alcohol.

4. The process of claim 2, wherein said solvent for lignin is an aromatic alcohol.

5. The process of claim 2, wherein said solvent for lignin is a ketone, an aldehyde, an ether, or a combination thereof.

6. The process of claim 1, wherein said solvent for lignin is a non-oxygenated alkane, non-oxygenated olefin, non-oxygenated aromatic hydrocarbon, or a combination thereof.

7. The process of claim 1, wherein said solvent for lignin is an ionic liquid.

8. The process of claim 1, wherein said solvent for lignin is water-soluble and, during step (b), forms a single phase with said water.

9. The process of claim 1, wherein said solvent for lignin, during step (b), forms a separate phase from said water or from a water-rich phase comprising said water.

10. The process of claim 1, wherein step (d) further comprises treatment of said separated cellulose-rich solids with sulfur dioxide and/or one or more acids.

11. The process of claim 10, wherein said one or more acids are selected from the group consisting of sulfurous acid, lignosulfonic acid, acetic acid, formic acid, and combinations thereof.

12. The process of claim 1, wherein step (d) further comprises treatment of said separated cellulose-rich solids with one or more enzymes.

13. The process of claim 1, said process further comprising bleaching said cellulose-rich solids prior to step (d) and/or as part of step (d).

14. The process of claim 1, said process further comprising bleaching said nanocellulose material during step (d) and/or following step (d).

15. The process of claim 1, wherein during step (d), said cellulose-rich solids are treated with a total mechanical energy of less than about 5000 kilowatt-hours per ton of said cellulose-rich solids.

16. The process of claim 1, wherein said crystallinity of said nanocellulose material is at least 60%.

17. The process of claim 1, said process further comprising hydrolyzing amorphous cellulose into glucose in step (b) and/or step (d), recovering said glucose, and optionally fermenting said glucose to a fermentation product.

18. The process of claim 1, said process further comprising recovering, fermenting, or further treating hemicellulosic sugars derived from said hemicellulose.

19. The process of claim 18, said process further comprising fermenting said hemicellulosic sugars to produce a monomer or precursor thereof; polymerizing said monomer to produce a polymer; and combining said polymer and said nanocellulose material to form a polymer-nanocellulose composite.

20. The process of claim 1, wherein said nanocellulose material is at least partially hydrophobic via deposition of at least some of said lignin onto a surface of said cellulose-rich solids during step (b), or via deposition of at least some of said lignin onto a surface of said nanocellulose material during step (d) or step (e).

* * * * *